United States Patent
Beran et al.

(10) Patent No.: US 6,183,128 B1
(45) Date of Patent: Feb. 6, 2001

(54) APPARATUS AND METHOD FOR DETERMINING PAPERBOARD THERMAL CONDUCTIVITY

(75) Inventors: Robert Lynn Beran, Covington; James Arthur Rule, Jr., Lexington, both of VA (US)

(73) Assignee: Westvaco Corporation, New York, NY (US)

(*) Notice: Under 35 U.S.C. 154(b), the term of this patent shall be extended for 0 days.

(21) Appl. No.: 09/304,225

(22) Filed: May 3, 1999

(51) Int. Cl.$^7$ .................................................. G01N 25/18
(52) U.S. Cl. ............................................. 374/44; 702/136
(58) Field of Search .................................. 374/44, 43, 29; 702/136

(56) References Cited

U.S. PATENT DOCUMENTS

| | | | |
|---|---|---|---|
| 3,662,587 | * | 5/1972 | Allen et al. ............................. 374/44 |
| 4,630,938 | * | 12/1986 | Piorkowska-Palczewska et al. ..................................... 374/44 |
| 4,929,089 | * | 5/1990 | Tshuchida ............................. 374/44 |
| 5,005,985 | * | 4/1991 | Piorkowska-Galeska et al. .... 374/44 |
| 5,112,136 | * | 5/1992 | Sakuma et al. ......................... 374/44 |
| 5,258,929 | * | 11/1993 | Tsuchida ................................ 374/44 |
| 5,622,430 | * | 4/1997 | Pletka et al. ........................... 374/44 |
| 5,667,301 | * | 9/1997 | Jurkowski et al. ..................... 374/44 |

OTHER PUBLICATIONS

Harvalik, Z. V., "A modified Fitch Thermal Conductivity System," The Review of Scientific Instruments, Vol. 18, No. 11 (Nov. 1947).*

Terada, T., N. Ito, & Y. goto, "Effective Thermal Conductivity of insulating Paper", Japan TAPPI, vol. 23, No. 5, pp. 191–197, 1969.

Terasaki, K. & K. Matsuura, The study of the Effective Thermal Conductivity of Papers for Temperature and Humidity, 2nd Report, Japan TAPPI, vol. 26, No. 10, pp. 511–515, 1972.

Kirk, L.A., & C. Tatlicibasi, "Measurement of Thermal Conductivity of Paper by a Heat Pulse Method", TAPPI, vol. 55, No. 12, pp. 1697–1700, Dec. 1972.

(List continued on next page.)

Primary Examiner—Diego Gutierrez
Assistant Examiner—Stanley J. Pruchnic, Jr.
(74) Attorney, Agent, or Firm—J. R. McDaniel; R. L. Schmalz

(57) ABSTRACT

This invention relates to an apparatus and method for determining paperboard thermal conductivity. Such structures of this type, generally, determine the thermal conductivity of a planar material, such as paperboard or insulating foams. The apparatus is designed to characterize the heat flow from a heated brass cylinder, through a flat paperboard sample, and into another brass cylinder. The brass cylinders are fully insulated, except at the sample interface. During the test, which is in a transient state, the hot mass loses energy, raising the temperature of the cooler mass as the two masses approach an intermediate equilibrium temperature. Knowing that the brass masses are fully insulated, except for the heat transfer interface, and knowing the physical properties of the masses, the only unknown in the mathematical model describing the experiment is the thermal conductivity, k, of the paperboard sample, which enables its determination.

5 Claims, 7 Drawing Sheets

OTHER PUBLICATIONS

Kerekes, R.J., "A simple method for determining the thermal conductivity and contact resistance of paper", TAPPI/Sep. 1980, vol. 63, No. 9, pp. 137–140.

Mark, R.E., "Handbook of Physical and Mechanical Testing of Paper and Paperboard", vol. 2; Marcel Dekker, 23 Thermal Properties, Jul. 31, 1984.

Seyed–Yagoobi, J.,K.H. Ng, L.S. Fletcher, "Thermal Contact Conductance of a Bone–Dry Paper Handsheet/Metal Interface", Journal of Heat Transfer, vol. 114, May 1992, pp. 326–330.

Asensio, M.C., J. Seyed–Yagoobi, & L.S. Fletcher, "Thermal Contact Conductance of a Moist Paper Handsheet/Metal Interface for Paper Drying Applications", Journal of Heat Transfer Tech Notes, vol. 115 (Nov. 1993) pp. 1051–1053.

"Standard Test Method for Steady–State Heat Flux Measurements and Thermal Transmission Properties by Means of the Guarded–Hot–Plate Apparatus[1]", ASTM Designation; C 177–97, pp. 1–22. (Jun. 1997).

* cited by examiner

LUMPED CAPACITY MODEL CHECK
LOWER MINUS UPPER POSITION TEMP (300°F)

THERMAL CONDUCTIVITY TEST
0.022 CALIPER, 63# BARE PAPERBOARD

THERMAL CONDUCTIVITY TEST
0.022 CALIPER, 63# BARE PAPERBOARD

THERMAL CONDUCTIVITY TEST
0.022 CALIPER, 63# BARE PAPERBOARD

THERMAL CONDUCTIVITY TEST
0.022 CALIPER, 63# BARE PAPERBOARD

APPARATUS AND METHOD FOR DETERMINING PAPERBOARD THERMAL CONDUCTIVITY

BACKGROUND OF THE INVENTION

1. Field of the Invention

This invention relates to an apparatus and method for determining paperboard thermal conductivity. Such structures of this type, generally, determine the thermal conductivity of a planar material, such as paperboard or insulating foams. The apparatus is designed to characterize the heat flow from a heated brass cylinder, through a flat paperboard sample, and into another brass cylinder. The brass cylinders are fully insulated, except at the sample interface. During the test, which is in a transient state, the hot mass loses energy, raising the temperature of the cooler mass as the two masses approach an intermediate equilibrium temperature. Knowing that the brass masses are fully insulated, except for the heat transfer interface, and knowing the physical properties of the masses, the only unknown in the mathematical model describing the experiment is the thermal conductivity, k, of the paperboard sample, which enables its determination.

2. Description of the Related Art

A number of devices are available, or have been reported, for the determination of thermal conductivity of planar materials. A device which takes two to three hours for a single test named the Fox 300 Heat Flo Meter was developed by Laser Corp. The cost to measure a single sample on that device is over $800 per sample.

A method for determining the thermal conductivity and contact resistance of paper has been proposed, but this method requires a large size sample to be wrapped around a cylinder. Exemplary of such prior art is an article to R. J. Kerekes, entitled "A Simple Method for Determining the Thermal Conductivity and Contact Resistance of Paper," TAPPI Journal, Vol. 63, No. 9, September 1980, pp. 137–140. The size of samples under current consideration for the present invention are not adequate for this type of test.

A planar and smaller version of such a test has been reported by Asensio and Seyed-Yagoobi. See, for example, M. C. Asensio et al., entitled "Thermal Contact Conductance of a Moist Paper Handsheet/Metal Interface for Paper Drying Application," *Journal of Heat Transfer*, Technical Notes, Vol. 115, November 1993, pp. 1051–1053 and J. K. Seyed-Yagoobi et al., entitled "Thermal Contact Conductance of a Bone-Dry Paper Handsheet/Metal Interface," *Journal of Heat Transfer*, Vol. 114, May 1992, pp. 326–330. This method, although adequate, has more of a focus on thermal contact resistance of paper on a metal interface for study of paper machine drying. Samples for this test must be cut to precise dimensions. This is not conducive to the current needs of the present invention. The test of a single sample on this apparatus has been reported to take up to eight hours to complete.

Thermal conductivity of small paperboard samples has been determined using a differential scanning calorimetry (DSC) device. Exemplary of such prior art is discussed by S. M. Marcus et al., entitled "Thermal Conductivity of Polymers, Glasses, and Ceramics by Modulated DSC," TA Instruments, Document TA-086. The sample size for these tests is approximately ¼ in. diameter. Even with the small sample size, a single test can take hours to perform and the small scale can raise questions when the nonuniformity of paperboard is of the same order of magnitude. Also, this is a "modulated" frequently-domain test where the thermal conductivity is backed out from repeated heating/cooling cycles. The size of the sample is simply too small to be representative of a paperboard packager length scales of interest.

There is an ASTM standard test for thermal conductivity and several experimental setups are described. See, for example, R. E. Mark, entitled *Handbook of Physical and Mechanical Testing of Paper and Paperboard*, Vol. 2, Chap. 23, "Thermal Properties," July 1984, pp. 241–279 and ASTM Standard Test Methods, C177-85 (1993) el, Summary of "Standard Test Method for SteadyState Heat Flux Measurements and Thermal Transmission Properties by Means of the Guarded-Hot-Plate Apparatus," 1997, ASTM, West Conshohucken, Pa. General features of the ASTM apparatus are shown in FIG. 2 on page 246, Nakagawa et al., in the Volume of Mark. This test falls into the category of a "steady state" device. It appears that the heat flux from one hot plate to another is the measured quantity and thermal conductivity is inferred from the experiment using Fourier's law.

Terasaki also uses a steady state method in which the sample is wrapped around a small diameter heated copper tube. See, for example, K. K. Terasaki et al., entitled "The Study of the Effective Thermal Conductivity of Papers for Temperature and Humidity, 2nd Report," *Japan TAPPI*, Vol. 26, No. 10, pp. 511–515, 1972. A schematic of the device is shown in FIG. 3 on page 248 of the R. E. Mark reference. The low-temperature-differential system consists of transferring heat from the heated tube, through the wrapped sample, to a controlled air environment. This apparatus is not exactly conducive to testing single plies of "hard to wrap" paperboard, polystyrene, and composite samples.

Terada discloses a method by which paperboard samples are studied in a controlled, low pressure, nitrogen environment condition in a steady-state experiment. See, for example, T. N. Terada et al., entitled "Effective Thermal Conductivity of Insulating Paper," *Japan TAPPI*, Vol. 23, No. 5, pp. 191–197, 1969. A schematic of the device is shown in FIG. 4 on page 248 of the R. E. Mark reference.

A "transient-state" experiment has been devised by Kirk and Tatlicibasi in which a flash power pack and flash tube are used as an energy source. See, for example, L. A. Kirk et al., entitled "Measurement of Thermal Conductivity of Paper by a Heated Pulse Method," *TAPPI*, Vol. 55, No. 12, pp. 1697–1700, 1972. A schematic of the device is shown in FIG. 5 on page 249 of the R. E. Mark reference. The thermal conductivity of the sample is backed out from the experiment by way of the sample's thermal diffusivity, $\alpha = k/(\rho C)$. The drawback of this approach is that the specific heat C and density $\rho$ for the sample must be known. This is not the case for the present invention, in which the density and specific heat of the known brass masses are needed, and held as constants in all tests of paperboard samples.

It is apparent from the above that there exists a need in the art for an apparatus which can easily, precisely and repeatably measure the thermal conductivity of a paperboard sample. It is the purpose of this invention to fulfill this and other needs in the art in a manner more apparent to the skilled artisan once given the following disclosure.

SUMMARY OF THE INVENTION

Generally speaking, this invention fulfills these needs by providing an apparatus for determining the thermal conductivity of paperboard, comprising a partially insulated, heated, metallic cylinder, a partially insulated, unheated, metallic cylinder located a predetermined distance away from the heated cylinder, a temperature monitoring means operatively connected to the heated and unheated cylinders, a temperature measurement means operatively connected to the temperature monitoring means, and a paperboard sample located substantially between the heated and unheated cylinders and in contact with the heated and unheated cylinders.

In certain preferred embodiments, the metallic cylinders are constructed of brass. Also, the temperature monitoring means includes thermocouples. Finally, the temperature measurement means is comprised of a differential temperature meter and a portable data logging computer.

In another further preferred embodiment, the apparatus is used to determine the thermal conductivity of planar material by characterizing the heat flow from the heated metallic cylinder, through the flat paperboard sample, and into the unheated cylinder.

The preferred apparatus, according to this invention, offers the following advantages: lightness in weight; ease of assembly and repair; excellent thermal conductivity measurement characteristics; good durability; and excellent economy. In fact, in many of the preferred embodiments, these factors of lightness in weight, ease of assembly and repair, excellent thermal conductivity measurement characteristics, and economy are optimized to an extent that is considerably higher than heretofore achieved in prior, known thermal conductivity measurement apparatus.

The above and other features of the present invention, which will become more apparent as the description proceeds, are best understood by considering the following detailed description in conjunction with the accompanying drawings, wherein like characters represent like parts throughout the several views and in which:

A BRIEF DESCRIPTION OF THE DRAWINGS

DETAILED DESCRIPTION OF THE INVENTION

Figure 1:
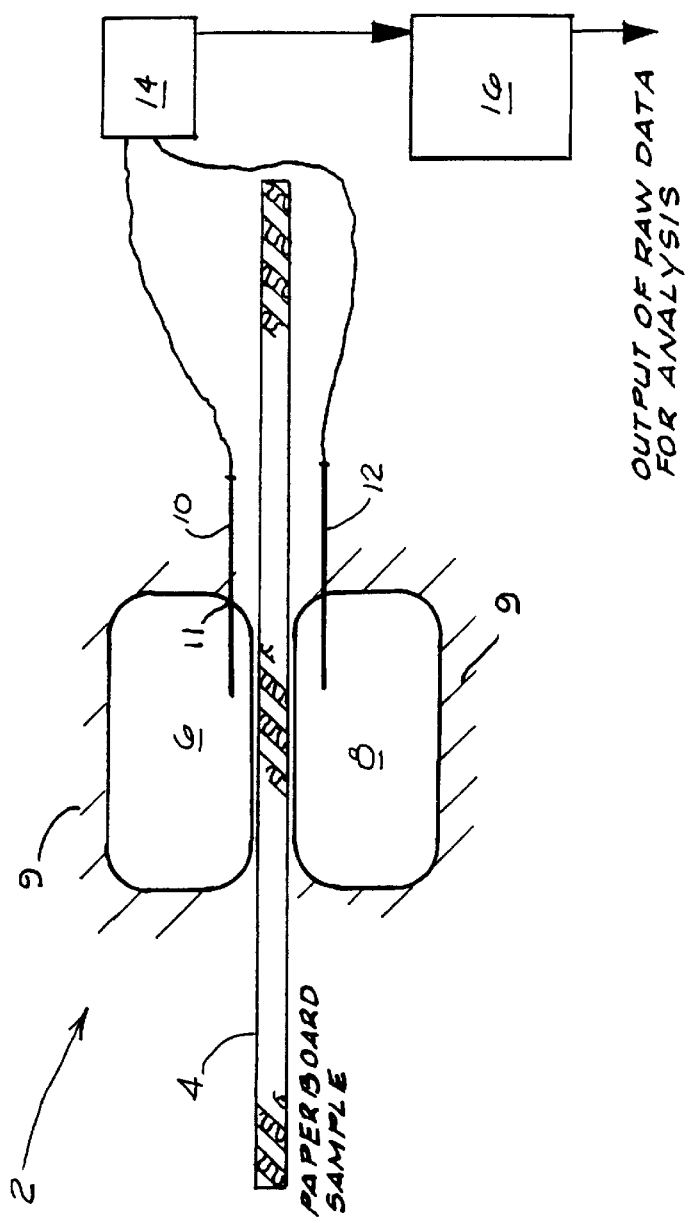
FIG. 1 is a schematic illustration of an apparatus for determining the thermal conductivity of paperboard, according to the present invention.

With reference first to FIG. 1, there is illustrated an advantageous environment for use of the concepts of this invention. FIG. 1 illustrates thermal conductivity apparatus 2. Apparatus 2 includes, in part, paper sample 4, hot brass cylinder 6, unheated brass cylinder 8, conventional insulation 9, conventional Type K thermocouples 10 and 12, holes 11, conventional differential temperature meter 14, and conventional data logging computer processor 16.

Apparatus 2 has been designed to allow heat transfer from a heated brass cylinder 6, through a paperboard sample 4, to an unheated brass cylinder 8. Each brass cylinder 6 and 8 is insulated, except at the interface, where the paperboard sample 4 is placed. As time goes by, the hot cylinder 6 gets cooler and the unheated cylinder 8 gets hotter, and ultimately, both cylinders 6 and 8 reach the same temperature. The thermal conductivity of the paperboard sample can be determined by monitoring the time-dependent temperature difference between the two cylinders 6 and 8 coupled with a thermodynamic model of the system. Each brass cylinder 6 and 8 weighs about 3¼ lb, is almost 3 in. in diameter, and about 2 in. high. There are two small holes 11 conventionally drilled into the sides of each cylinder, each nominally 0.295 in. from the flat faces. A Type K thermocouple 10 and 12 is placed into the hole nearest the paperboard sample 4. A conventional Differential Temperature Meter 14 is used as a continuous analog output of the temperature difference between the two cylinders 6 and 8.

The hot cylinder 6 is heated to approximately 165° F. Both the hot and unheated cylinders 6 and 8, respectively, are fitted into conventional insulation 9 designed to keep unaccounted-for heat transfer losses to a minimum, except at the paperboard interface. The paperboard sample 4 is sandwiched between the hot and cold cylinders 6 and 8, respectively, and a conventional portable computer processor 16 is used to log the temperature difference as the hot cylinder 6 cools and the ambient cylinder 8 gets warmer. The heat transfer process is logged for about 30 minutes.

A computer program was used for logging the transient experimental temperature difference data. See, for example, a copy of the computer program at end of this section. A conventional Data Translation DT2801 12-bit a/d card was used to digitize the analog signal. A voltage data reading was recorded every 5 seconds, but 20 a/d conversions were averaged to form up each data reading. The 20 conversions took only 59 msec to execute and this modification greatly improved the data stability compared to making only one a/d conversion at every time step.

The raw data is then analyzed for determination of thermal conductivity. Consider one-dimensional conduction heat transfer between a lumped energy capacity hot cylinder 6 at $T_1$ across the heat transfer interface resistance $R_{th}$ to an ambient cylinder 8 at $T_2$ shown in the sketch below:

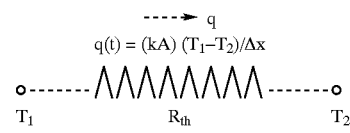

The process is time-dependent in $T_1$ and $T_2$ because no energy is added to the system, and the total energy of the system stays constant. Since the heat transfer depends on the temperature difference, q will also be a function of time. At any time, the energy in block 1 is $E_1(t)=\rho_1 C_1 V_1 T_1$ and in block 2 the energy is $E_2(t)=\rho_2 C_2 V_2 T_2$ where $\rho$ is density, C is specific heat and V is volume. The two cylinders 6 and 8 are identical so the energy expressions can be simplified as $E_1(t)=\rho CV\, T_1$ and $E_2(t)=\rho CV\, T_2$. Since both blocks are insulated, total energy is conserved, and time-independent in Equation 1:

$$\frac{d}{dt}(E_1 + E_2) = 0 \qquad \text{(Eq. 1)}$$

The heat transfer leaving the hot block equals the heat transfer arriving at the cold block in Equation 2:

$$\frac{dE_1(t)}{dt} = -q(t) \wedge \frac{dE_2(t)}{dt} = +q(t) \qquad \text{(Eq. 2)}$$

Positive heat flow as shown in the sketch raises the energy of block 2. Consider that the initial conditions are known in Equation 3:

$$T_1(t=0)=T_{10} \text{ and } T_2(t=0)=T_{20} \qquad \text{(Eq. 3)}$$

Combine (Eq. 2) and (Eq. 3) and substitute expressions for $E_1$ and q to get in Equation 4:

$$\frac{d}{dt}[\rho C V T_1] + \frac{T_1 - T_2}{(\Delta x / k A)} = 0 \qquad \text{(Eq. 4)}$$

Both $T_1$ and $T_2$ are functions of time. The total energy is constant at any time and equal to the initial total energy in Equation 5:

$$E_{total} = \rho C V T_{10} + \rho C V T_{20} = \rho C V T_1(t) + \rho C V T_2(t) \qquad \text{(Eq. 5)}$$

Solving for $T_2(t)$ in Equation 6:

$$T_2(t) = T_{10} + T_{20} - T_1(t) \qquad \text{(Eq. 6)}$$

Substitute (Eq. 6) into (Eq. 4) to arrive at Equation 7:

$$\frac{d}{dt}[\rho C V T_1] + \frac{2T_1}{(\Delta x / k A)} - \frac{(T_{10} + T_{20})}{(\Delta x / k A)} = 0 \qquad \text{(Eq. 7)}$$

Now let $\theta = 2 T_1 - (T_{10} + T_{20})$ so that $d\theta = 2dT_1$ and substituting and separating (Eq. 7) gives Equation 8:

$$\frac{d\theta}{\theta} = \frac{-2dt}{(\Delta x / k A)(\rho C V)} \qquad \text{(Eq. 8)}$$

Integrating (Eq. 8) from 0 to t gives Equation 9:

$$\ln\left(\frac{\theta}{\theta_0}\right) = \frac{-2t}{(\Delta x / k A)(\rho C V)} \qquad \text{(Eq. 9)}$$

At $t=0$, $\theta_0 = 2 T_{10} - (T_{10}+T_{20}) = T_{10} - T_{20}$

Using the energy balance $(T_{10}+T_{20}) = T_1 + T_2$, substituting back into (Eq. 9), and solving for k in Equation 10:

$$k = \left[-\frac{\Delta x \rho C V}{2tA}\right] \ln\left[\frac{\Delta T}{\Delta T_0}\right] \qquad \text{(Eq. 10)}$$

where: $\Delta x$ is the thickness of the paperboard sample, ft,
$\rho$ is the density of the brass cylinder, lb/ft$^3$,
C is the specific heat of the brass cylinder, Btu/lbm° F.
V is the volume of a single brass cylinder, cuft,
A is the heat transfer interface area, ft$^2$,
T is the time elapsed from the initial condition, hr, and
$\Delta T$ is the temperature difference, F, and k is the thermal conductivity, Btu/(hr ft° F.).

The significance of this expression is that at any time during the transient experiment, a value for k is fully described by the current temperature difference, initial temperature difference, and lumped heat capacity properties. For a perfect experiment, and if k is independent of temperature, then an identical result for k will be obtained at each data-taking time step.

It is desired to extend the thermal conductivity modeling from analyzing a single data point each time to modeling the entire experiment and determining an effective thermal conductivity for the entire transient.

We wish to fit an exponential curve as shown in Equation 11:

$$\Delta T = b e^{-at}, \qquad \text{(Eq. 11)}$$

where a and b are constants that result in the best fit of the experimental data. Take the natural log of both sides as shown in (Eq. 11):

$$\ln(\Delta T) = -at + \ln(b) \qquad \text{(Eq. 12)}$$

Simplify (Eq. 12) with new variables y*, m*, and b*:

$$y^* = m^* t + b^*, \qquad \text{(Eq. 13)}$$

where t is in minutes for consistency with the data-taking scheme. A linear least-squares fit can now be determined for the data set. Using a value m* for the best-fit slope and (Eq. 10), the thermal conductivity is determined by:

$$k = -\frac{60 m * \Delta x \rho C V}{2A} \qquad \text{(Eq. 14)}$$

where: $\Delta x$ is the thickness of the paperboard sample, ft,
$\rho$ is the density of the brass cylinder, lb/cuft,
C is the specific heat of the brass cylinder, Btu/lbm° F.,
V is the volume of a single brass cylinder, cuft,
A is the heat transfer interface area, ft$^2$, and
k is the thermal conductivity, Btu/(hr ft° F.).

The analytical approach to determine paperboard thermal conductivity depends on the hot mass or cylinder being at a uniform initial temperature, and both masses or cylinders being at a relatively uniform temperature throughout the transient process. Preliminary tests on the apparatus were made in order to verify these assumptions.

Figure 2:
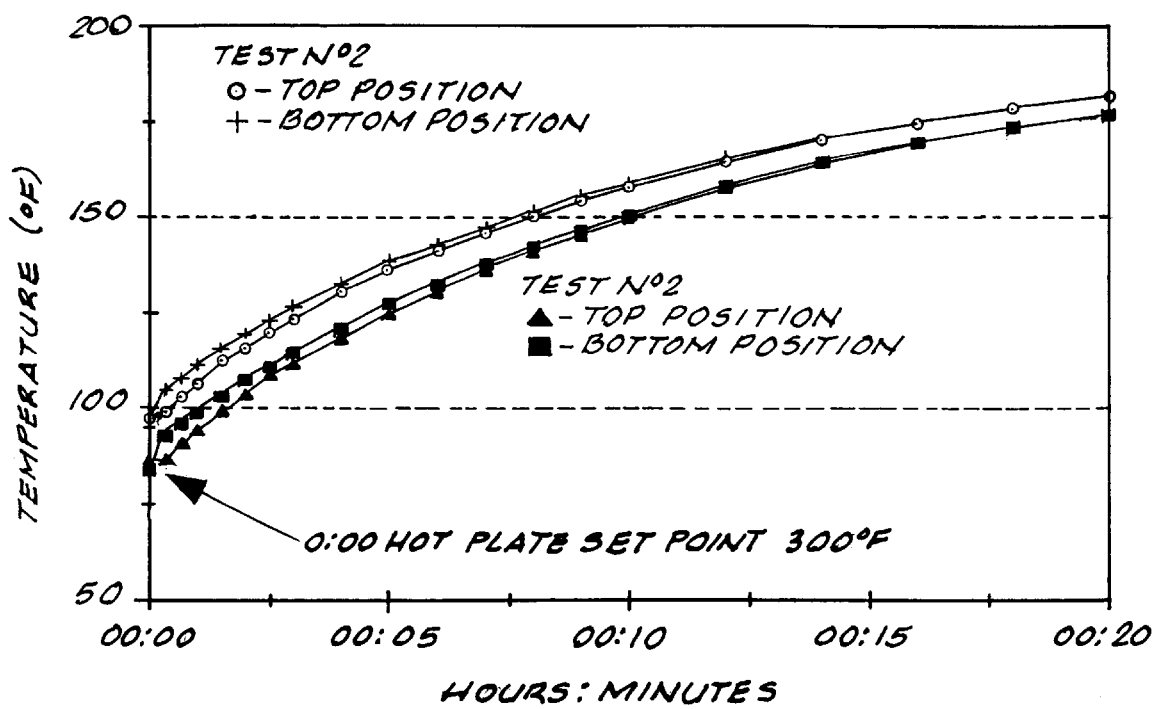
FIG. 2 is a graphical illustration of temperature, ° F., versus time, in minutes, for a brass block test for a lumped capacity.
Figure 3:
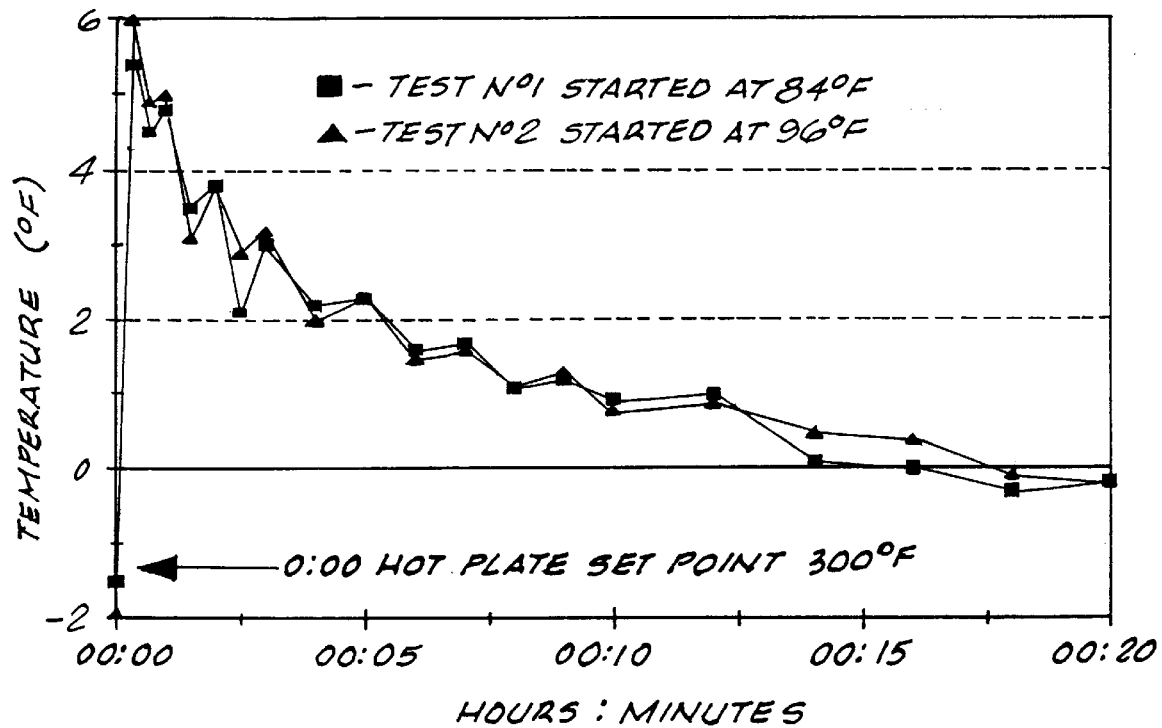
FIG. 3 is a graphical illustration of temperature, ° F., versus time, in minutes, for a lumped capacity model check.

It was determined that heating the hot mass on a Model 1900 Thermolyne hot plate set at 300° F. for about 10 minutes would result in a good uniform temperature. To verify this, both thermocouples were placed in the small holes of a single brass mass as it was heated on the hot plate. Temperatures were recorded by hand throughout the heating at temperatures of 250, 300, 350, and 450° F. The best heating to temperature was at the 300° F. setting as shown in FIG. 2. At this setting, the hot block was uniform to within less than 1° F. in 10 minutes as shown in FIG. 3.

Figure 4:
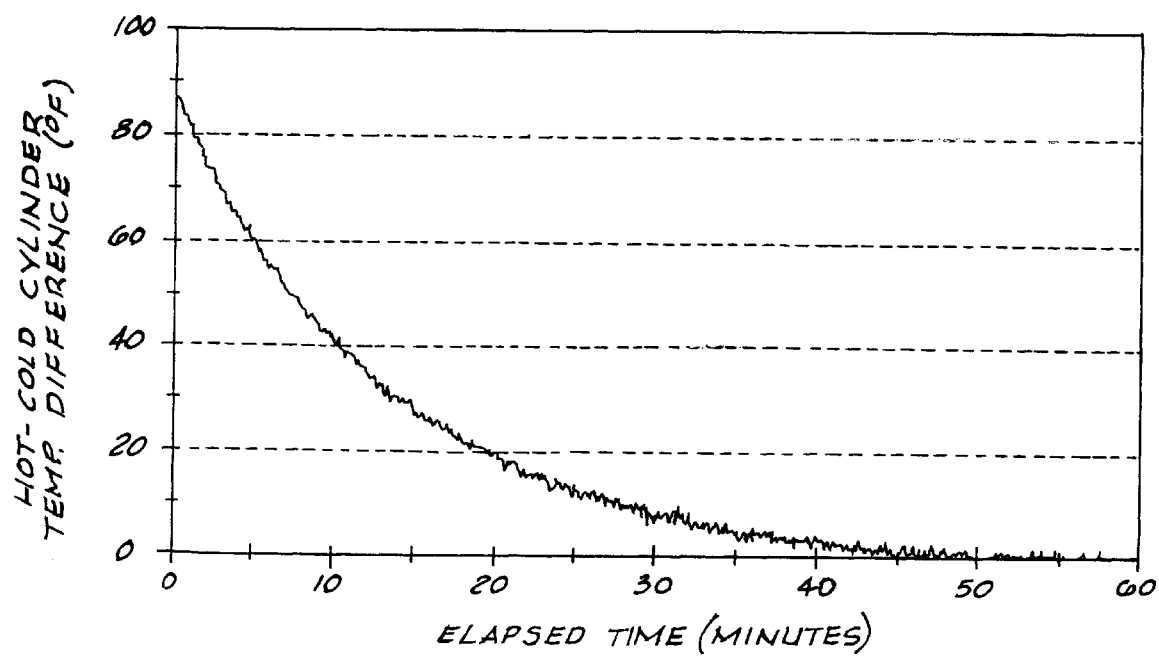
FIG. 4 is a graphical illustration of hot-cold cylinder temperature difference, ° F., versus elapsed time, in minutes, for a thermal conductivity test.
Figure 5:
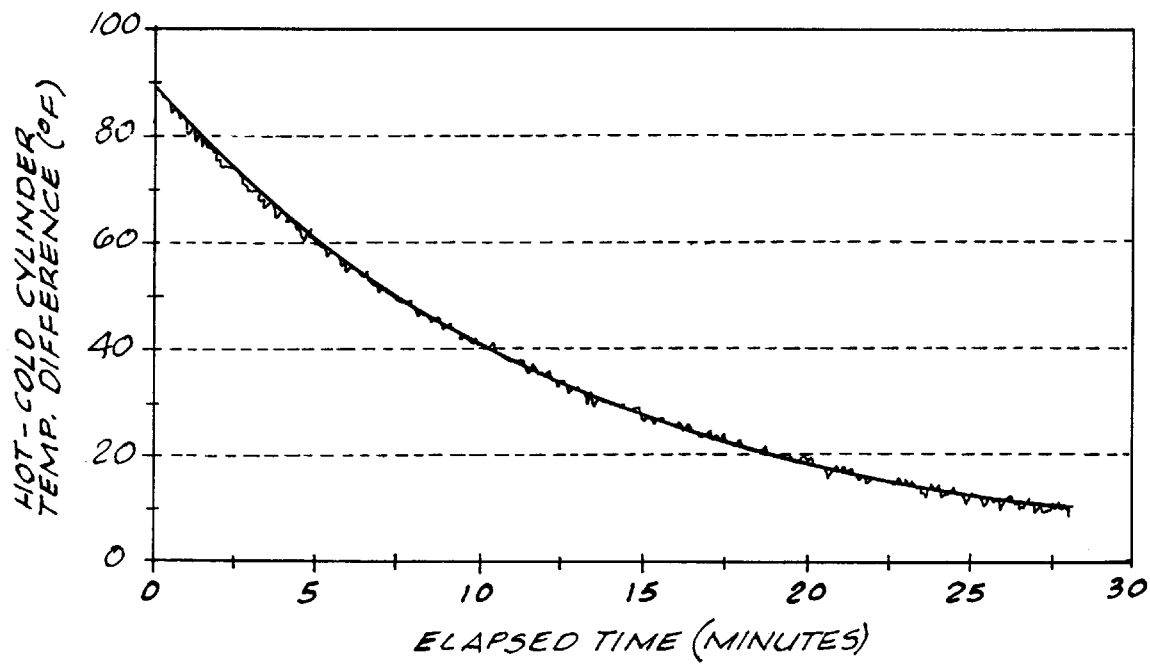
FIG. 5 is a graphical illustration of the hot-cold cylinder temperature difference, ° F., versus elapsed time, in minutes, for a thermal conductivity test.

Only the first 335 data points, or 28 minutes, from the raw data plotted in FIG. 4 was used for exponential curve fitting. The graphical fit for the 28 minute transient is shown in FIG. 5, and it is outstanding. Even the worst examples of curve-fitting for the first 6 samples were considered very good. TABLE 1, below, tabulates the raw data early in the transient and the thermal conductivity value determined from the exponential fit. For the 63 lb paperboard sample, thermal conductivity was determined to be 0.0384 Btu/hr ft° F.

(0.0664 W/m° C.), which is equivalent to an R-value of 0.0477 hr ft²° F./Btu for this 0.022 caliper sample.

TABLE 1

| 0.022 sample thickness (in.) | Thermal Conductivity Result from Exponential Fit | |
|---|---|---|
| 488.2 block density (lb/cuft) | 0.0384 thermal conductivity | (B/hr*ft**F) |
| 0.088 block specific heat (Btu/lb ° F.) | 0.0684 thermal conductivity | (W/m ° C.) |
| 0.00671 block volume (cuft) | 0.0477 R-value | (hr*ft² ° F./Btu) |
| .032405 heat trans area (sqft) | | |
| 89.5 initial temp difference (° F) from exponential fit | | |

| Experiment (sec) | Experiment Time (min) | (mv) | Temp Difference (° F.) | Thermal Conductivity (B/hr*ft**F) | Thermal Conductivity (W/m ° C.) | R-value (t/k) (hr*ft² ° F./Btu) |
|---|---|---|---|---|---|---|
| 5.0 | 0.08 | 6277 | 89.16 | 0.0230 | 0.0398 | 0.0798 |
| 10.1 | 0.17 | 6184 | 87.75 | 0.0578 | 0.1000 | 0.0317 |
| 15.2 | 0.25 | 6137 | 87.05 | 0.0540 | 0.0935 | 0.0339 |
| 20.2 | 0.34 | 6094 | 86.41 | 0.0514 | 0.0889 | 0.0357 |
| 25.3 | 0.42 | 6098 | 86.46 | 0.0403 | 0.0698 | 0.0455 |
| 30.3 | 0.51 | 5961 | 84.41 | 0.0570 | 0.0987 | 0.0321 |
| 35.3 | 0.59 | 5981 | 84.72 | 0.0459 | 0.0794 | 0.0399 |
| 40.3 | 0.67 | 5961 | 84.42 | 0.0428 | 0.0741 | 0.0428 |
| 45.4 | 0.76 | 5875 | 83.13 | 0.0480 | 0.0830 | 0.0382 |
| 50.4 | 0.84 | 5944 | 84.16 | 0.0360 | 0.0623 | 0.0509 |
| 55.4 | 0.92 | 5843 | 82.65 | 0.0424 | 0.0734 | 0.0432 |
| 60.4 | 1.01 | 5680 | 80.20 | 0.0535 | 0.0927 | 0.0342 |
| 65.4 | 1.09 | 5718 | 80.78 | 0.0462 | 0.0800 | 0.0397 |
| 70.5 | 1.18 | 5829 | 82.43 | 0.0344 | 0.0595 | 0.0533 |
| 75.5 | 1.26 | 5608 | 79.11 | 0.0482 | 0.0833 | 0.0381 |
| 80.6 | 1.34 | 5693 | 80.39 | 0.0392 | 0.0679 | 0.0467 |
| 85.6 | 1.43 | 5540 | 78.09 | 0.0469 | 0.0812 | 0.0391 |
| 90.6 | 1.51 | 5642 | 79.63 | 0.0380 | 0.0658 | 0.0482 |
| 95.6 | 1.59 | 5521 | 77.82 | 0.0431 | 0.0746 | 0.0425 |
| 100.6 | 1.68 | 5530 | 77.95 | 0.0405 | 0.0701 | 0.0453 |
| 105.6 | 1.76 | 5469 | 77.04 | 0.0419 | 0.0724 | 0.0438 |
| 110.7 | 1.85 | 5495 | 77.43 | 0.0386 | 0.0667 | 0.0475 |
| 115.7 | 1.93 | 5365 | 75.48 | 0.0434 | 0.0751 | 0.0423 |
| 120.7 | 2.01 | 5382 | 75.72 | 0.0408 | 0.0706 | 0.0449 |
| 125.7 | 2.10 | 5265 | 73.97 | 0.0447 | 0.0773 | 0.0410 |
| 130.7 | 2.18 | 5248 | 73.72 | 0.0437 | 0.0756 | 0.0419 |
| 135.8 | 2.26 | 5260 | 73.89 | 0.0416 | 0.0720 | 0.0441 |
| 140.8 | 2.35 | 5259 | 73.88 | 0.0401 | 0.0695 | 0.0457 |

Figure 6:
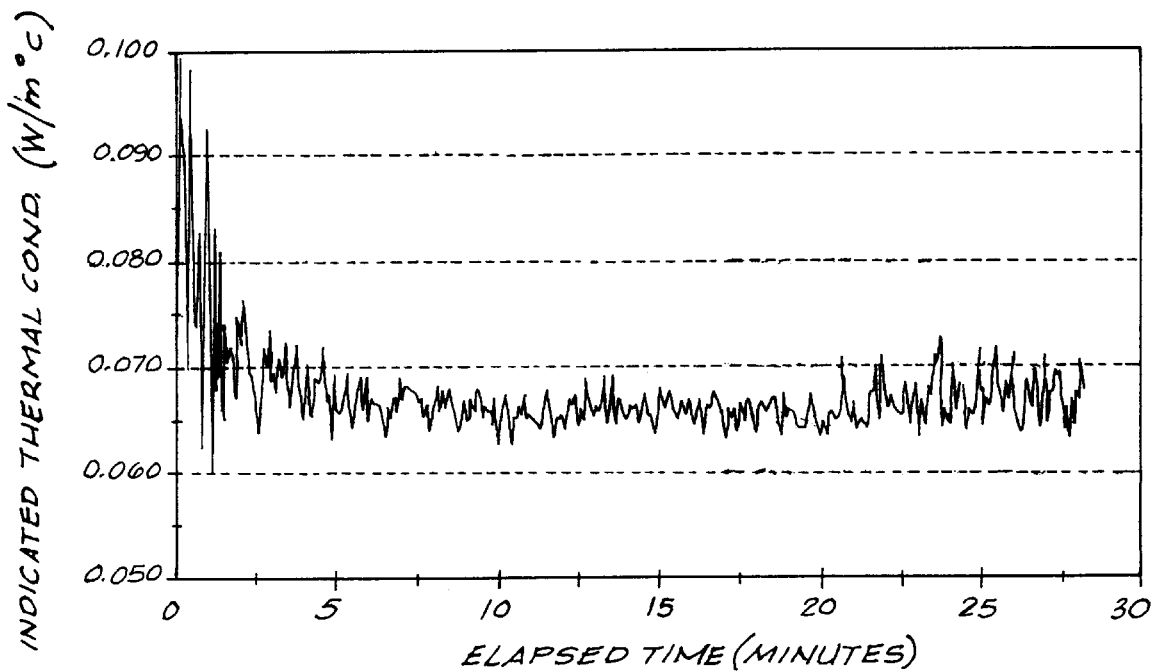
FIG. 6 is a graphical illustration of indicated thermal conductivity, in W/m° C., versus elapsed time, in minutes.
Figure 7:
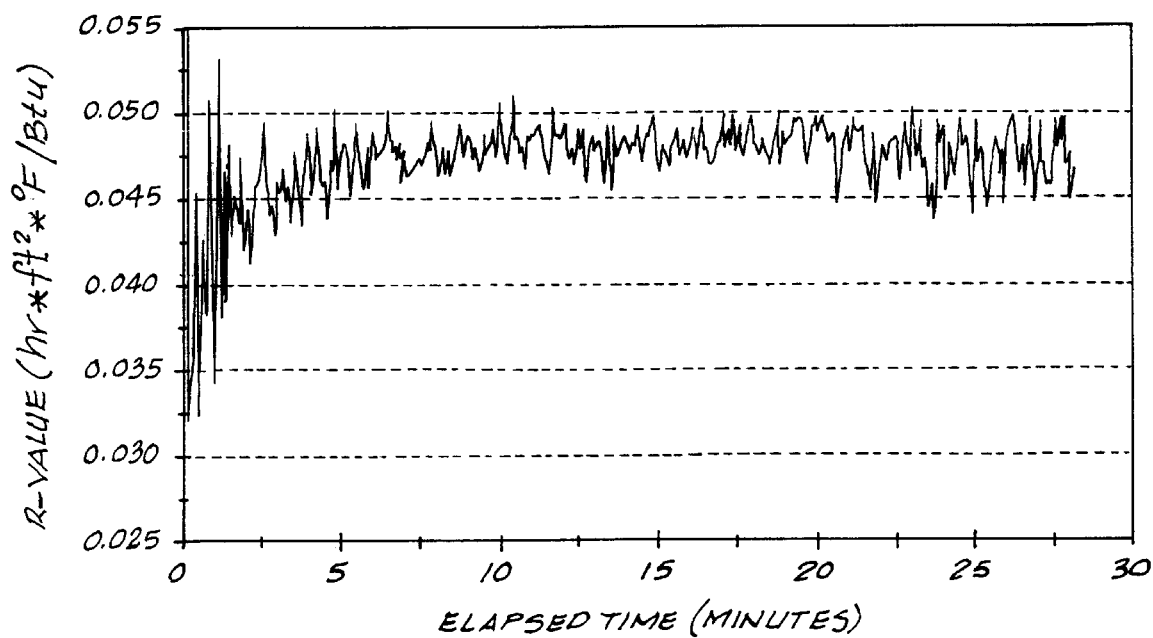
FIG. 7 is a graphical illustration of R-value, in hr×ft$^2$×° F./Btu, versus elapsed time, in minutes.

How does this compare to the indicated values of thermal conductivity for each data point? FIGS. 6 and 7 depict the instantaneous values of k and R-value for the transient. The result is satisfying since the majority of instantaneous thermal conductivity values are in the 0.065–0.070 W/m° C. range compared to the exponential-fit value of 0.0664 W/m° C. The same positive result is observed in the R-value comparison. The beauty of the exponential-fit approach is to wash out the noisy results of the instantaneous values and eliminate the need for arbitrary averaging.

Once given the above disclosure, many other features, modifications or improvements will become apparent to the skilled artisan. Such features, modifications or improvements are therefore, considered to be a part of this invention, the scope of which is to be determined by the following claims.

A:A18: 5
A:B18:+A18/60
A:C18: 6869.8
A:D18:+A$4+C18/10000*(A$5−A$4)
A:G18:−A$7/12*A$8*A$9*A$10/2/(B18/60)/A$11*@LN(D18/A$12)
A:H18:+G18/0.5779
A:I18:+A$7/12/G18
A:K18: @LN(D18)
A:L18: @EXP(K$384)*@EXP(K$383*B18)

Mathematical Coding for the First Row of the Thermal Conductivity Spreadsheet.

A:K383: @SLOPE(K18 . . . K352,B18 . . . B352)
A:L383: '=m star
A:K384: @INTERCEPT(K18 . . . K352,B18 . . . B352)
A:L384: '=b star
A:K385: @EXP(K384)
A:L385: '=dTo Mathematical Coding for the Analytical Curve-Fit Variables m* and b*.

What is claimed is:

1. A method for determining the thermal conductivity of paperboard, wherein said method is comprised of the steps of:

heating a partially insulated, metallic cylinder having a first density, specific heat, volume, and interface area;

measuring a first temperature of said heated metallic cylinder and a partially insulated, unheated metallic cylinder having said first density, specific heat, volume, and interface area;

placing a paperboard sample having a first thickness substantially between said heated and said ambient temperature cylinders;

measuring a second temperature of said heated and unheated cylinders;

determining a temperature difference between said heated and unheated cylinders; and determining a thermal conductivity of said paperboard sample, according to the equation:

$$k = -\frac{60 m^* \Delta x \rho C V}{2A}$$

where: Δx=the thickness of the paperboard sample, ft,
ρ=the density of the cylinders, lb/cuft,
C=the specific heat of the cylinders, Btu/lbm °F.,
V=the volume of a single cylinders, cuft,
A=the heat transfer interface area, ft$^2$,
k=the thermal conductivity, Btu/(hr ft °F.), and
m*=the mass of the cylinders, lb.

2. The method, as in claim 1, wherein said heated metallic cylinder is further comprised of:

brass.

3. The method, as in claim 1, wherein said unheated metallic cylinder is further comprised of:

brass.

4. The method, as in claim 1, wherein said temperature measuring steps are further comprised of the step of:

monitoring said temperature with a thermocouple; and measuring said temperature with a temperature meter and a portable, data logging computer.

5. The method, as in claim 4, wherein said temperature meter is further comprised of:

a differential temperature meter.

\* \* \* \* \*